United States Patent [19]

Kukes et al.

[11] Patent Number: 4,590,174

[45] Date of Patent: May 20, 1986

[54] OLEFIN METATHESIS CATALYST

[75] Inventors: Simon G. Kukes; Robert L. Banks, both of Bartlesville, Okla.

[73] Assignee: Phillips Petroleum Company, Bartlesville, Okla.

[21] Appl. No.: 651,510

[22] Filed: Sep. 11, 1984

Related U.S. Application Data

[62] Division of Ser. No. 517,298, Jul. 26, 1983, Pat. No. 4,517,401.

[51] Int. Cl.$^4$ .......... B01J 31/02; B01J 27/14; B01J 27/02; B01J 27/06
[52] U.S. Cl. .................. 502/219; 502/168; 502/210; 502/211; 502/220; 502/228
[58] Field of Search ............ 502/168, 210, 211, 219, 502/220, 228

[56] References Cited

U.S. PATENT DOCUMENTS

Re. 31,443 11/1983 McDaniel et al. ............ 502/219 X
3,940,346 2/1976 Zuech ..................... 252/430
4,089,930 5/1978 Kittrell et al. ................ 502/219 X
4,443,330 4/1984 Nongbri .................. 502/219 X

FOREIGN PATENT DOCUMENTS 57-140652 8/1982 Japan ..................... 502/219
806108 12/1978 U.S.S.R. ................. 502/220

*Primary Examiner*—D. E. Gantz
*Assistant Examiner*—William G. Wright
*Attorney, Agent, or Firm*—Howard D. Doescher

[57] ABSTRACT

Olefins are converted into other olefins having different numbers of carbon atoms by contact with a catalyst comprising an inorganic refractory oxide support containing at least one of tungsten oxide and molybdenum oxide and a promoting amount of at least one methylating agent under conditions suitable for the methylating agent compounds to promote the activity of tungsten and molybdenum oxides for the disproportionation reaction.

10 Claims, No Drawings

4,590,174

OLEFIN METATHESIS CATALYST

This application is a division of application Ser. No. 517,298, filed July 26, 1983, now U.S. Pat. No, 4,517,401.

BACKGROUND OF INVENTION

This invention relates to the disproportionation (metathesis) of olefins. In accordance with one aspect, this invention relates to a catalyst suitable for use in the disproportionation of olefinic hydrocarbons. In accordance with another aspect, this invention relates to a process for the disproportionation of olefinic hydrocarbons. In accordance with a further aspect, this invention relates to a catalyst suitable for use in the disproportionation of olefins comprising at least one of molybdenum oxide and tungsten oxide, an inorganic refractory oxide support, and at least one methylating agent. In accordance with a further aspect, this invention relates to a catalyst suitable for use in the disproportionation of olefins comprising a support and at least one of molybdenum oxide and tungsten oxide promoted with at least one methylating agent. In accordance with another aspect, this invention relates to a process for the disproportionation of olefinic hydrocarbons with a disproportionation catalyst as hereinbefore described under conditions of temperature and pressure which effect disproportionation of the feed.

The disproportionation, or metathesis, of olefins is a reaction in which one or more olefinic compounds are transformed into other olefins of different molecular weights. The disproportionation of an olefin with itself to produce an olefin of a higher molecular weight and an olefin of a lower molecular weight can also be referred to as a self-disproportionation. For example, propylene can be disproportionated to ethylene and cis-, and trans-2-butene. Another type of disproportionation involves the cross-disproportionation of two different olefins to form still other olefins. An example would be the reaction of one molecule of 2-butene with one molecule of 3-hexene to produce two molecules of 2-pentene.

By the term "disproportionation" or "metathesis" throughout this specification is meant the conversion of the feed olefinic (or unsaturated) hydrocarbon to a mixture of olefinic (or unsaturated) hydrocarbons having different numbers of carbon atoms than the feed hydrocarbons.

Among the catalysts that have been developed for disproportionation are those comprising inorganic refractory oxides containing a catalytic amount of at least one of molybdenum oxide and tungsten oxide. The present invention is based upon the discovery of a way to improve the activity of such a catalyst.

Accordingly, an object of this invention is to provide a method for the conversion of olefins.

Another object of this invention is to provide a catalyst for the conversion of olefins.

Still another object of this invention is to provide a method for converting olefins to olefins having different numbers of carbon atoms than the feed hydrocarbons.

Still another object is to provide a method for improving the activity of a disproportionation catalyst for the conversion of olefins into olefins having different numbers of carbon atoms than the feed hydrocarbons.

Other aspects, objects and the several advantages of the invention will be apparent to one skilled in the art upon reading the disclosure including a detailed description of the invention and the appended claims.

SUMMARY OF INVENTION

In accordance with the present invention, a disproportionation (metathesis) catalyst comprising an inorganic refractory oxide containing a catalytically effective amount of at least one of molybdenum oxide and tungsten oxide is improved by contacting the catalyst with a promoting amount of at least one methylating agent under conditions suitable for the methylating agent to promote the activity of molybdenum and tungsten oxides.

Further, in accordance with a specific embodiment of the present invention, a disproportionation (metathesis) catalyst comprising an inorganic refractory oxide, such as silica, containing a catalytically effective amount of tungsten oxide is improved by contacting the tungsten oxide catalyst with a promoting and activating amount of at least one methylating agent, such as dimethyl sulfate, under conditions suitable for the methylating agent to promote the activity of tungsten oxide.

Also according to the invention, a process is provided for the disproportionation of an olefinic hydrocarbon by contacting the same with a disproportionation catalyst as hereinbefore described under conditions of temperature and pressure which effect disproportionation of the feed.

The inorganic refractory oxide comprises solid inorganic oxide support usually containing a major proportion of alumina or silica. Such materials are commonly known as refractory oxides and include, for example, silica, alumina, magnesia-alumina, silica-alumina, titania-alumina, zirconia-alumina, alumina-titania-zirconia, thoria, aluminum phosphate, zirconium phosphate, calcium phosphate, magnesium phosphate, thorium phosphate, and titanium phosphate. Preferred refractory metal oxides are silica refractory oxides, i.e., refractory oxides containing a substantial proportion of silica, e.g., at least 90 percent by weight of silica, preferably at least 99 percent of silica can be used. Generally, the refractory oxide has a surface area of at least 10 m$^2$/g and preferably the surface area is from about 25 m$^2$/g to 800 m$^2$/g.

Molybdenum oxide and tungsten oxide can be combined with the refractory oxide support in any conventional manner such as dry mixing, impregnation from a diluent, ion-exchange or the like. The oxides can be added directly or in the form of molybdenum or tungsten compounds that can be converted to oxides by calcination.

Preferred combinations of the above support materials with the oxides of molybdenum and tungsten promoter materials include (1) silica or thoria promoted by the oxide, or a compound convertible to an oxide by calcination, of tungsten or molybdenum; (2) alumina promoted by an oxide, or compound convertible to an oxide by calcination, of molybdenum or tungsten; and (3) one or more of the group aluminum phosphate, zirconium phosphate, calcium phosphate, magnesium phosphate, thorium phosphate or titanium phosphate promoted by one or more of an oxide of molybdenum or tungsten, or by a compound of molybdenum or tungsten convertible to an oxide by calcination.

The solid component of the catalysts can be in any conventional catalytic shape or size, depending upon the type of conversion in which it is to be utilized. For example, in fixed bed catalyst systems, the solid composite can be in the form of spheres, pellets, extrudates, agglomerates, and the like. In slurry catalyst systems, the solid can be in the form of relatively small particles or in the form of a powder.

To be effective in the present catalyst system, the above-described component of the catalysts is activated at elevated temperatures, generally in flowing air. The activation of the catalysts is accomplished at a temperature of from about 300° to about 800° C. for a period of several minutes to several hours or longer. When the solid component of the catalyst system is tungsten oxide on silica, a convenient and economical treatment is in the temperature range of 400°–700° C. for 0.5 to 20 hours or longer. In some cases the activation using an oxygen-containing gas can be followed by treatment, also at elevated temperatures, with other treating gases such as carbon monoxide, hydrogen, and the like.

The oxide of molybdenum or tungsten is preferably combined with the inorganic oxide solid support in a high positive oxidation state, e.g., hexavalent molybdenum or hexavalent tungsten. The proportion of the molybdenum or tungsten oxide combined with the inorganic oxide support can be varied, but generally the inorganic oxide solid contains at least 0.1 percent by weight of the oxide of molybdenum or tungsten with amounts from about 0.2 percent to about 30 percent by weight being preferred, although still larger (major) proportions of molybdenum or tungsten oxide can be used. The weight percent referred to is based on the combined weights of the support and the metal.

The methylating agent can be combined with the thus prepared catalyst in any suitable manner. For example, the catalyst is impregnated with a liquid diluent containing the methylating agent. After impregnation the catalyst is then heated in an inert atmosphere, such as nitrogen or argon, to remove the liquid diluent. The temperature employed in removing the diluent and activating can vary widely; however, temperatures in the range of about 400° C. to about 800° C. are currently preferred. If desired, the methylating agent can be applied to the catalyst in a reaction zone by spraying or otherwise contacting the catalyst. It is also contemplated that the methylating agent can be introduced along with olefin feed for contacting with the catalyst.

The benefits provided by the methylating agent treatment are adversely affected if the catalyst is later exposed to an oxidative atmosphere, especially at elevated temperatures. Accordingly, preferably the catalyst is maintained under a substantially inert atmosphere after the methylating treatment.

Examples of methylating agents that can be used according to the invention include dimethyl sulfate, dimethylsulfoxide, trimethyloxonium tetrafluoroborate, methyl iodide, and methyl bromide, and the like, and mixtures thereof.

The optimum amounts of methylating agent employed can readily be determined by routine experimentation. Generally, the methylating agent should be used in an amount in the range of about 0.1 to about 20 weight percent, preferably about 5 to about 15 weight percent, based on the total weight of the metal oxide and support prior to the addition of the methylating agent.

The promoted catalyst can be used in disproportionation reactions in a conventional manner. The reaction temperature can vary depending upon the catalyst and feed(s) employed, but will be sufficient to effect disproportionation. Typically, the disproportionation is carried out at a temperature in the range of about 20° to about 600° C.

The disproportionation reaction can be carried out by contacting the olefins to be disproportionated with the catalyst in the liquid phase or the gas phase, depending on structure and molecular weight of the olefins, temperature and pressure.

Olefins applicable for use in the process of the invention are nontertiary, nonconjugated acyclic mono- and polyenes having at least 3 carbon atoms per molecule including cycloalkyl, cycloalkenyl, and aryl derivatives thereof; cyclic and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3–30 carbon atoms per molecule and with such cyclic olefins having 4–30 carbon atoms per molecule. Nontertiary olefins are those olefins wherein each carbon atom, which is attached to another carbon atom by means of a double bond, is also attached to at least one hydrogen atom. Internal olefins are preferred.

Some specific examples of acyclic olefins suitable for reactions of this invention include propylene, 1-butene, 2-butene, 1-pentene, 2-pentene, 1-hexene, 1,4-hexadiene, 2-heptene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 2-methyl-4-octene, 4-vinylcyclohexane, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclodecatriene, 1,4,7,10-cyclododecatetraene, 6-methyl-6-ethylcyclooctadiene-1,4, and the like, and mixtures thereof.

The pressure during the disproportionation reaction may vary between wide limits. Pressures between 0.1 and 500 atm. are suitable; preferred pressures are between 0.5 and 250 atm. If possible, the process should be operated at a pressure which is atmospheric or nearly atmospheric so that no vacuum or pressure apparatus is required.

If the reaction is carried out in the liquid phase, solvents or diluents for the reactants may be used. Aliphatic saturated hydrocarbons (e.g., pentane, hexane, cyclohexane, dodecane) and aromatic hydrocarbons such as benzene and toluene are suitable. If the reaction is carried out in the gaseous phase, diluents such as aliphatic hydrocarbons (e.g., methane, ethane) and/or inert gases (e.g., nitrogen, argon) can be present. Preferably the disproportionation reaction is effected in the substantial absence of reactive materials such as water and oxygen.

The length of time during which the olefinically unsaturated compounds to be disproportionated are contacted with the catalyst depends upon several factors such as the activity of the catalyst, temperature, pressure, and structure of the olefinically unsaturated compound to be disproportionated. Contact time can conveniently vary between 5 seconds and 24 hours, although longer and shorter contact times may be used. The contact time needed to obtain a reasonable yield of disproportionated products depends on the factors mentioned above.

The process of the invention is effected batchwise or continuously, with fixed catalyst beds, slurried catalysts, fluidized beds or by using any other conventional contacting technique. The solid disproportionation catalysts are employed in any appropriate form, for example, as powders, flakes, pellets, spheres or extrudates.

The olefinic products of the invention, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following example.

In the example, the tungsten oxide content of the catalyst was 6 weight percent based on the total weight of tungsten oxide and silica. The catalyst was prepared by impregnating high surface area silica with 0.0727 gram of ammonium metatungstate (($NH_4$)$_2$$W_4O_{13}$·8-$H_2O$) per gram of silica. The impregnation was accomplished by treating the silica with an aqueous solution of the ammonium metatungstate. The impregnated silica was dried and calcined in air at 500° C. to convert the metatungstate to the oxide. A −20+40 mesh sieve fraction was obtained for use as described below.

Both runs were made by passing a propylene feed through a vertical tubular quartz reactor (1 cm in diameter and 25 cm in length) positioned in a temperature-controlled electric furnace. In each run the reactor contained a bed of the designated catalyst. A thermocouple was positioned in the catalyst bed to monitor reaction temperature. Prior to each run the catalyst was activated by heating at 600° C. in flowing nitrogen for 0.5 hours.

The propylene feed was of a polymerization grade as sold by Phillips Petroleum Company of Bartlesville, Okla. The propylene feed was pretreated with activated Alcoa H151 alumina and activated magnesia prior to the metathesis. The feed was passed downwardly through the vertically oriented tubular reactor. Reaction product analyses were made by gas-liquid chromatography (glc) employing a Hewlett-Packard model 5880A chromatograph having a ⅜ inch by 20 ft. column packed with 19% BMEE +1% squalene on 60/80 Chrom P. Analysis was carried out isothermally at a temperature of 30° with a helium carrier gas flow rate of about 20 mL/min.

EXAMPLE

The reactor was loaded with 2 g of 6% $WO_3$·$SiO_2$ catalyst, heated to 600° C. for 1 hour in air, purged with $N_2$ for 30 minutes, then allowed to cool to 412° C., then propylene flow of about 100 mL/min. at atmospheric pressure introduced. Samples were collected at various time intervals for 90 minutes and analyzed for conversion of propylene to ethylene and butenes. Results are presented in the Table.

Propylene feed was discontinued, the catalyst calcined in air for 30 minutes at 600° C., then cooled to room temperature. Once the reactor was cool, 2 mL of dimethylsulfate was sprayed over the catalyst, unabsorbed liquid allowed to drain, then the catalyst was heated to 600° C. for 90 minutes under a gentle flow of nitrogen. The reactor was then cooled to 412° C. and propylene feed at a rate of about 100 mL/min. at atmospheric pressure introduced. Samples were collected and analyzed as above. Results are presented in the Table.

TABLE

| Catalyst | Conversion, % time, minutes | | | | | |
|---|---|---|---|---|---|---|
| | 5 | 15 | 30 | 45 | 60 | 90 |
| Untreated | 1.5 | 3.5 | 4.1 | 4.6 | 5.2 | 6.0 |
| ($CH_3O$)$_2$$SO_2$ added | 5.1 | 8.5 | 10.6 | 12.3 | 13.5 | 15.4 |

The results of these experiments demonstrate the enhanced propylene conversion achieved with dimethylsulfate treated $WO_3$·$SiO_2$ catalyst.

What is claimed is:

1. A process for preparing a disporportionation catalyst comprising admixing a catalytically effective amount of a calcined and activated catalyst consisting essentially of at least one metal oxide selected from molybdenum oxide and tungsten oxide and a support containing a major proportion of silica or alumina with a promoting amount of a methylating agent selected from the group consisting of dimethyl sulfate, dimethylsulfoxide, trimethyloxonium tetrafluorborate, methyl iodide, and methyl bromide, and subjecting same to inert atmospheric conditions for said methylating agent to promote the activity of said calcined molybdenum and tungsten oxides for the disporportionation of olefins.

2. A process according to claim 1 wherein said methylating agent is added to said calcined catalyst in solution and the resulting composition is dried under an inert atmosphere at a temperature in the range of about 400° C. to about 800° C.

3. A process according to claim 2 wherein said catalytic amount of said metal oxide is in the range of about 1 to about 10 percent of the combined weights of said metal oxide and said support prior to the addition of the methylating agent.

4. A process according to claim 3 wherein the methylating agent is employed in an amount in the range of about 0.1 to about 20 weight percent based on the weight of the calcined metal oxide-refractory oxide combination prior to the addition of the methylating agent.

5. A process according to claim 4 wherein said metal oxide is $WO_3$ and said refractory oxide is $SiO_2$.

6. A process according to claim 5 wherein said methylating agent is dimethyl sulfate.

7. In a process for the preparation and activation by calcination of an olefin disproportionation catalyst consisting essentially of at least one of molybdenum oxide and tungsten oxide and a support containing a major proportion of silica or alumina prior to use, the improvement wherein the calcined catalyst is contracted with a promoting amount of a methylating agent selected from the group consisting of dimethyl sulfate, dimethylsulfoxide, trimethyloxonium tetrafluoroborate, methyl iodide, and methyl bromide, and then the promoted catalyst is maintained in an inert atmosphere until placed in use.

8. A process according to claim 7 wherein said methylating agent is dimethyl sulfate.

9. A process according to claim 7 wherein the amount of methylating agent employed ranges from about 0.1 to about 20 weight percent based on total weight of calcined catalyst.

10. A process according to claim 7 wherein said calcined catalyst in tungsten oxide on silica and said methylating agent is dimethyl sulfate.

* * * * *

UNITED STATES PATENT AND TRADEMARK OFFICE
CERTIFICATE OF CORRECTION

PATENT NO. : 4,590,174

DATED : May 20, 1986

INVENTOR(S) : SIMON G. KUKES and ROBERT L. BANKS

It is certified that error appears in the above-identified patent and that said Letters Patent is hereby corrected as shown below:

Col. 7, line 7, "contracted" should be ---contacted---.

Col. 8, line 2, "in" should be ---into---.

Col. 8, line 10, "in" should be ---is---.

Signed and Sealed this

Thirtieth Day of September 1986

[SEAL]

Attest:

DONALD J. QUIGG

Attesting Officer

Commissioner of Patents and Trademarks